United States Patent [19]

Sandine et al.

[11] Patent Number: 4,547,373
[45] Date of Patent: Oct. 15, 1985

[54] WINE PREPARATION WITH NEW STRAINS OF *LEUCONOSTOC OENOS*

[75] Inventors: William E. Sandine; David A. Heatherbell, both of Corvallis, Oreg.

[73] Assignee: State of Oregon acting by and through the State Board of Higher Education for and on behalf of Oregon State University, Corvallis, Oreg.

[21] Appl. No.: 521,988

[22] Filed: Aug. 11, 1983

[51] Int. Cl.⁴ ............................ C12G 1/00; C12N 1/20
[52] U.S. Cl. ...................................... 426/15; 435/253
[58] Field of Search ........................... 426/15; 435/253

[56] References Cited

PUBLICATIONS

Kishkovskaya et al–Chem. Abst., vol. 93, (1980), p. 148050g.

Bur'yan et al–Chem. Abst., vol. 95, (1981), p. 95411h.

*Primary Examiner*—Sam Rosen
*Attorney, Agent, or Firm*—Kolisch, Hartwell & Dickinson

[57] ABSTRACT

Strains of *Leuconostoc oenos* capable of carrying out malolactic fermentation in wines at relatively low temperatures and in wines having relatively high acidity.

2 Claims, No Drawings

WINE PREPARATION WITH NEW STRAINS OF *LEUCONOSTOC OENOS*

BACKGROUND AND SUMMARY OF THE INVENTION

This invention relates to malolactic bacteria, and more particularly to a novel strain of *Leuconostoc oenos* capable of carrying out malolactic fermentation (MLF) in wines at relatively low temperatures and having relatively low pH values, i.e., high acidity.

Grapes grown in the northwestern United States and in the cooler wine-growing regions of Europe are generally lower in sugar and higher in acid than grapes grown in warmer climates. This is due to a number of factors, including the maturity of the grapes at harvest, the climate under which the grapes are grown, the cultivation practices utilized, soil conditions, fermentation procedures, etc. The low sugar content and high acidity of such grapes often results in the production of wines with harsh tastes.

Principal acids of the grape are tartaric and malic acid, and while the proportion of the total acidity contributed by malic acid is variable, when acidity is high, it may account for as much as half the total amount. Malolactic fermentation or MLF refers to the conversion of malic acid to lactic acid and carbon dioxide occurring in wine as the result of the metabolic activity of certain strains of lactic acid bacteria. The fermentation reduces the total acidity of the wine, stabilizes the wine biologically by assuring that MLF will not take place in the bottle, and further increases the flavor complexity of the wine. There are three genera of lactic acid bacteria that are principally associated with MLF in wines, and of these, the most predominant genus is Leuconostoc.

Pure culture inoculation of wine with *Leuconostoc oenos* offers several advantages to the wine maker. It enables the wine maker to stimulate MLF in musts, or wines, in a rapid and predictable manner, and provides assurance that a dependable bacterium is dominant in the fermentation. Bacteria such as *L. oenos* ML-34 and *L. oenos* PSU-1 are used commercially in locations such as California for such reasons. However, these organisms are not well suited to more northerly climes by reason of the low temperature conditions existing during wine production, and the low pH of the wines being processed, which render the bacteria relatively inactive.

The instant invention conerns novel strains of *Leuconostoc oenos* (Er-1a and Ey-2d) which exhibit the ability to carry out MLF in musts and wines rapidly and predictably with the wines at relatively low temperature, i.e., 20° C. or below. A further feature of the invention concerns a bacterial strain having the ability to carry out MLF in wines having high acidity, i.e., low pH.

*L. oenos* strains Er-1a and Ey-2d were isolated from wines provided by wineries in the northwest of the United States by making pour plates of diluted wine samples and through successive incubations and removal of isolated bacterial colonies, thus to obtain a multiplicity of strains which were further evaluated. Strains Er-1a and Ey-2d are included in the culture collection of the American Type Culture Collection, 12301 Parklawn Drive, Rockville, Maryland, under ATCC designation 39401 and 39402, respectively.

The culture medium used in the growth of the bacteria was basically a modified Rogosa broth medium (MRV-8). It consisted of 2.0% Tryptone (Bacto), 0.5% yeast extract (Yeast Products Inc.), 0.5% peptone (Bacto), 0.5% glucose (Sigma), 0.3% fructose (Sigma), 0.2% L-malic acid (Sigma), and 0.005% Tween 80 (Baker). The medium base was a 1:4 dilution of vegetable juice (V-8 juice) which was initially centrifuged in a Beckman Model J2-21 centrifuge at 10,000×g for 15 minutes to remove tomato pulp. The supernatant was filtered through analytical filter papers (Schleicher & Schuell #597) and then filtered again through glass microfiber filters (Whatman GFA). This resulted in a medium which did not exhibit sedimentation. The pH of the medium was adjusted to 5.5 with 6N NaOH being a Corning 125 digital pH meter. The same broth medium was used to make an agar medium for plating purposes by the addition of 12 g/L Davis agar.

The above broth medium was sterilized by autoclaving at 121° C., 15 psi for 15 minutes. In the initial isolation of strains from wine samples, an appropriate aliquot of filter-sterilized cycloheximide solution (Sigma) was added just prior to pouring to achieve a concentration of approximately 50 ppm in the agar medium.

Bacteria were isolated by making pour plates of 0.5 ml aliquots of diluted wine samples in an agar medium prepared as above set forth. The medium was used as an initial isolation medium to prevent yeast and mold contamination and overgrowth of slow-growing malolactic organisms. Samples contaminated with large numbers of wine yeasts (as evidenced by obvious turbidity) were initally subjected to a sterile centrifuge treatment. Centrifugation at 1000 RPM for 15 minutes removed most of the yeast cells. The clarified supernatant was then plated in similar fashion.

Plates were incubated under carbon dioxide tension of approximately 8% at 28°–30° C. for three to four days. Typical lactic acid bacterial colonies developed that were elliptical in shape and creamy white in color. Microscopic examination showed them to be gram positive cocci in pairs and chains. Representative isolated colonies of varying size and color hue were removed aseptically from the agar in small blocks (approximately 64 cubic mm). These were then suspended and disrupted in sterile screw-capped tubes containing 10 ml of the modified Rogosa broth medium. Following growth at 30° C. for three to four days, cultures were streaked on agar medium plates for isolation. When satisfied that distinct pure colonies had developed, they were again examined, inoculated as stab cultures in an agar medium prepared as set forth above, and stored at 4° C. Cultures were routinely incubated either in the Gas Pak Carbon Dioxide System (BBL) or in a controlled environment carbon dioxide incubator (National Appliance Co.) at 30° C. for three to four days. Stab cultures were transferred every three to four months to maintain viability.

*L. oenos* strains Er-1a and Ey-2d were characterized as strains of *L. oenos* according to a number of parameters. Both strains were checked for their ability to metabolize malic acid and both were determined to be active in decarboxylating L-malate. The strains were gram stained, checked for presence of catalase and surface growth on agar stab cultures. Cultures of the strains were then checked for dextran production from sucrose, ammonia production from arginine and production of lactic acid from glucose. These determinations were made following accepted procedures (Garvie, 1967; Pilone and Kunkee, 1972). The taxonomic properties of the two strains are summarized in Table I.

TABLE I

Characterization Profile

| Morphology | Cocci, pairs and chains |
|---|---|
| Gram reaction | + |
| Heterofermentative | + |
| Facultative anaerobes | + |
| Gas from glucose | + |
| Catalase reaction | − |
| Growth on agar stab surface | +/− |
| Dextran from sucrose | − |
| Ammonia from arginine | − |
| Lactic acid from glucose | + |

Carbohydrate fermentation patterns were quite similar in the two strains. Both strains fermented glucose, fructose, maltose, ribose, cellobiose, trehalose, salicin and esculin. Arabinose was utilized by both to some extent. Sorbose was utilized primarily by Er-1a. Mannitol and raffinose were weakly used by Ey-2d, and xylose was weakly used by Er-1a. Table II sets forth carbon and energy sources utilized by the two strains.

TABLE II

| Carbon Source | % Growth rate compared to glucose | |
|---|---|---|
| | Er-1a | Ey-2d |
| L-arabinose | 57 | 31 |
| Cellobiose | 115 | 93 |
| Fructose | 109 | 103 |
| Glucose | 100 | 100 |
| Lactose | 0 | 0 |
| Maltose | 98 | 106 |
| Mannitol | 0 | 15 |
| Raffinose | 0 | 5 |
| Salicin | 85 | 72 |
| Ribose | 111 | 96 |
| Sucrose | 0 | 0 |
| Trehalose | 87 | 112 |
| Xylose | 5 | 0 |
| D-arabinose | 39 | 42 |
| Galactose | 110 | 0 |
| Glycerol | 0 | 0 |
| Rhamnose | 0 | 0 |
| D-mannose | 0 | 0 |
| L-sorbose | 89 | 5 |
| Esculin | 93 | 89 |

The modified Rogosa culture medium described above was found to produce optimum growth rate of the strains in comparison to other culture media, which is consistent with the identification of the strains as wine Leuconostoc, since it has been demonstrated that such organisms grow best in a medium containing vegetable juice (V-8 juice) supplemented with glucose and fructose (Amachi, 1969, 1975; Garvie and Mabbit, 1967; Ingraham et al., 1960; Kunkee, 1967; Radler, 1975; Yoshizumi, 1975). By way of example, a broth medium as described above inoculated with bacteria strain Er-1a was determined to have a bacteria cell number initially of $1 \times 10^6$ CFU/ml. Such culture was incubated at 30° C. for four days on a Multi-MagneStir (Lab-Line Scientific, Inc.) at its lowest setting. Viable cell counts were determined daily for four days. After four days, the number of cells counted approximated $3 \times 10^8$ CFU/ml, and increase of greater than 0.5 log units per day.

In making this determination, cell counts were made using a micro-drop technique. It is well documented that Leuconostoc oenos is capable of forming long chains of cells (Beelman et al., 1980; Pilone and Kunkee, 1972). Such chains have been observed with regularity in gram stains of our cultures. Long chains containing numerous cells may produce only one macrocolony; therefore, the possibility of erroneously low counts is quite real. For enumeration, 1.0 ml of sample was aseptically blended with a Waring blender in chilled 0.1% (w/v) peptone (Bacto) diluent (99 ml) at high speed for 60 seconds to break up the chains of cocci (Martley, 1972). The blended sample was then serially diluted in sterile 0.1% peptone. Each dilution was dispensed in four separate 0.025 ml micro-drops with an Oxford Micro-Doser repetitive pipette onto pre-dried (48 hour ambient temperature) plates of the above-described agar medium, at pH 5.5. Cell counts were determined by averaging the colony counts of the four drops and multiplying by the appropriate dilution factor. Accuracy of counts is thereby increased and the need for duplicate plating is avoided. Plates were always incubated at 30° C. under carbon dioxide tension for three to five days before enumeration.

The carbohydrate fermentation patterns set forth in Table II were determined by the following method. A culture was grown in 100 ml of the above described broth medium and centrifuged at 7000 RPM for ten minutes. The pellet resulting was washed in 100 ml of 0.1% peptone water and spun again. The pellet was resuspended in 10 ml of 0.1% peptone water for use as inoculum. Screw-capped tubes containing 5 ml of the broth medium described above but lacking tomato juice, glucose, and fructose, and further including 0.5% of the membrane-filtered sugar to be tested, received a 2% culture inoculum. Incubation was at 30° C. Sugars tested included L-arabinose, D-arabinose, cellobiose, fructose, glucose, lactose, maltose, mannitol, raffinose, ribose, sucrose, trehalose, xylose, galactose, glycerol, rhamnose, D-mannose, L-sorbose, salicin and esculin. Due to the limited solubility, salicin and esculin were prepared in 0.2% concentration. Uninoculated media were used as negative controls.

A specific growth rate was determined for each carbohydrate. Spectrophotometric analysis was performed at periodic intervals for 96 hours using a Perkin-Elmer 35 Spectrophotometer at 600 nm. The specific growth rate, k, was determined using the formula:

$$k = \frac{2.303 (\log b - \log a)}{t}$$

where "a" and "b" are the optical density readings at two sampling times during logarithmic growth, and "t" is the time elapsed. Where necessary, cultures were diluted to remain within an absorbance range of approximately 0 to 0.4, the range within which Beer's Law is functional. The specific growth rates thus determined were compared to the growth rate for glucose as a carbon source. All growth was expressed as a percentage growth rate compared to glucose, which was considered to be 100%.

The general characteristics noted for strains Er-1a and Ey-2d are similar to those of L. oenos as described by previous investigators (Garvie, 1967; Pilone and Kunkee, 1972; Beelman et al., 1977) as well as Bergey's Manual of Determinative Bacteriology (Buchanan et al., 1974).

Studies were performed to determine the ability of L. oenos stains Er-1a and Ey-2d to ferment malic acid in a Pinot Noir wine at varying temperatures, and to compare the fermentation ability of these strains with conventional commercially available strains, i.e., L. oenos PSU-1 ("Leucostart" obtained from Tri Bio Laboratories, State College, PA), and L. oenos ML-34 (obtainable from a culture collection at University of California, Davis). The wine utilized was a new wine made from Pinot Noir grapes grown in Oregon. The wine was analyzed for degree Brix (soluble solids by refractometer, g/100 g as sucrose), total acidity (T.A.—g/100 ml as tartaric acid), volatile acidity (V.A.—by Cash stream distillation apparatus as g/100 ml acetic acid), pH (Corning Model 125 pH Meter), and alcohol (ebulliometer vol. %).

Table III below sets forth the results obtained in an analysis of the new wine.

TABLE III

| Soluble Solids (°Brix) | pH | T.A. | Alcohol |
|---|---|---|---|
| 0 | 3.49 | 0.80 | 10.9% |

The wine was dispensed (200 ml) into 250 ml Erlenmeyer flasks and autoclaved for 12 minutes at 121° C. After being autoclaved and cooled to room temperature (25° C.), the wine was analyzed and the following data obtained:

TABLE IV

| pH | T.A. | V.A. |
|---|---|---|
| 3.34 | 0.80 | 0.023 |

Sterilization of the wine was performed to ensure that any difference in the change in the composition of the volatile compounds that would occur between the inoculated samples and the uninoculated control was caused by the added bacteria and not by any other microorganism contained in the wine.

Measurements were made to determine relative malate levels in various wine samples, with the wine samples maintained at 20° C., 15° C., and 8° C. Prior to being inoculated with bacteria, the Erlenmeyer flasks containing the wine samples were placed in incubators at these respective temperatures to equilibrate with the incubator temperature before inoculation.

Cultures for inoculation for the temperature trials were grown in MRV-8 broth (pH 5.5) in 16 mm, screw-capped, glass tubes incubated under $CO_2$ (BBL GasPak $CO_2$ system. BBL Cockeysville, MD) at 30° C. After 35 hours the tubes had reached maximum turbidity and were refrigerated at 6° C. Approximately 20 hours later, the various wine samples were inoculated with 1% (v/v) of these cultures and placed back into the incubator. An uninoculated wine sample served as a control at each temperature.

The wines inoculated with the various bacterial strains and incubated as indicated were periodically analyzed by paper chromatography (Kunkee, 1968) for the disappearance of malic acid and for the formation of lactic acid. The activity of the malolactic cultures could be followed quite closely by measuring the approximate size of the malate spot and recording its change. Variation in the size of the malate spot of the same sample from chromatogram to chromatogram could be mostly eliminated by dividing its approximate size (width- × height) by the size of the malate spot of the uninoculated control. This produced a quantitative comparison which was used as an approximate measure of the activity of the cultures in the temperature trials. When the malate spot had disappeared on the paper chromatogram, it was assumed that malolactic fermentation was complete, although it is recognized that some activity does continue thereafter for a few days.

The study performed indicated that MLF at 20° C. was completed, in the case of *L. oenos* Er-1A and Ey-2d, within 21 days. In the case *L. oenos* PSU-1, MLF was completed at 83 days, and in the case of ML-34, MLF was completed at 144 days.

At 15° C., no significant decrease in malate concentration was noted after 12 months in wines fermented with *L. oenos* ML-34 and *L. oenos* PSU-1. The wine sample inoculated with *L. oenos* Ey-2d completed MLF in slightly less than 6 months. In the case of *L. oenos* Er-1a, at the end of one year the malate level detected was approximately ¼ the original malate level in the wine.

At 8° C., none of the strains completed MLF within 12 months. However, *L. oenos* Ey-2d did produce a malate level in the final wine which was approximately ⅛ the original malate level of the wine.

Additional trials were performed to show the effects of decreasing pH (increasing acidity) on the ability of *L. oenos* Er-1a and Ey-2d to ferment malate. *L. oenos* ML-34 and *L. oenos* PSU-1 were also employed in the trials.

In the trials, 16 mm, screw-capped, glass tubes were filled with MRV-8 broth (10 ml) adjusted with 8N tartaric acid (Sigma) before autoclaving (at 121° C., 15 min.). The pH values were determined before inoculation with 1% mature cultures, grown at 30° C. in MRV-8 broth (pH 4.6) for 4 days in 16 mm, screw-capped, glass tubes. The malate concentrations in the media were assayed enzymatically according to the method described by McCloskey (1980). For the enzymatic assay, glutamic oxaloacetic transaminase (#G-2751), NAD (#N-8881), and L-glutamic acid (#G-1251) were obtained from Sigma; malate dehydrogenase (#4426) and glycine (#3570) were obtained from Calbiochem (Calbiochem-Behring Corp., La Jolla, CA). The absorbance was read at 340 nm on a Beckman DU spectrophotometer model 2000, which was equipped with a Gilford 2000 absorbance recorder, solid state power supply and digital read-out provided by Update Instrument, Inc., Madison, WI.

These trials indicated that, with all *L. oenos* strains at a pH of 4.0 in a MRV-8 broth at 20° C., substantially complete fermentation of malate had occurred in 5 days or less. At a pH of 3.0, however, while strains ML-34, PSU-1, and Ey-2d were substantially inactive, *L. oenos* Er-1a reduced malate parts after 20 days from an original ppm of 2200 to less than 500.

A Chardonnay wine was prepared by harvesting Chardonnay grapes in Corvallis, Oregon, the grapes at harvest time having a °Brix of 17.4, a T.A. of 1.24 and a pH of 3.04. The fruit was crushed and destemmed, and pressing with a Willmes bag press produced a yield of 140 gallons per ton. The juice so produced was settled for 24 hours, at 4° C., racked from the settlings, and inoculated with 1% of Champagne yeast (Vi-A-Dri, Scott Labs, Santa Rosa, CA; *Saccharomyces bayanus* U.C.D. #595). The new wine was allowed to settle for 48 hours to remove the bulk of the yeast lees and racked. The Chardonnay wine was fermented at 13° C. for 26 days. The wine was then racked from the bulk yeast lees.

An analysis made of this new wine indicates the following: Alcohol 9.4%; T.A. 1.11; pH 3.06; malate 5650 mg/L.

The wine was divided into several duplicate lots in glass carboys and put into a room with a constant temperature of 18° C. before being inoculated with prepared bacterial cultures. Bacterial cultures were prepared from Er-1a, Ey-2d, ML-34 and PSU-1. These cultures were grown in MRV-8 broth (pH 4.6) at 30° C. until maximum growth was achieved (about 4 days). At this time the cultures were inoculated into a grape juice medium prepared from one volume of grape juice, one volume of distilled water, 0.05% yeast extract (Difco Laboratoratories, Detroit, MI) adjusted to a pH of 3.6 with 1 N NaOH. The cultures were grown in the grape juice medium at 27° C. until the malic acid disappeared, as determined by paper chromatography (Kunkee, 1968). At this point the bacterial cultures were ready for wine inoculation.

Samples of the new Chardonnay wine were inoculated with 1% bacterial starter cultures. After inoculation room temperature was maintained at between 16° and 18° C. The total acidity and pH of the wine samples were determined weekly, and completion of malolactic fermentation was also determined by disappearance of the malate spot on paper chromatograms. The following table indicates results obtained:

TABLE V

| | Er-1a | | Ey-2d | | ML-34 | | PSU-1 | |
|---|---|---|---|---|---|---|---|---|
| Days | T.A. | pH | T.A. | pH | T.A. | pH | T.A. | pH |
| 0 | 1.12 | 3.09 | 1.12 | 3.09 | 1.12 | 3.09 | 1.12 | 3.09 |
| 9 | 1.06 | 3.09 | 1.08 | 3.09 | 1.11 | 3.08 | 1.11 | 3.08 |
| 16 | 0.99 | 3.13 | 1.02 | 3.12 | 1.09 | 3.09 | 1.09 | 3.09 |
| 23 | 0.93 | 3.18 | 0.99 | 3.16 | 1.09 | 3.11 | 1.09 | 3.09 |
| 31 | 0.85 | 3.23 | 0.94 | 3.19 | 1.07 | 3.14 | 1.06 | 3.14 |
| 37 | 0.82 | 3.23 | 0.90 | 3.18 | 1.06 | 3.14 | 1.03 | 3.13 |
| 50 | 0.75* | 3.24 | 0.84 | 3.20 | 1.02 | 3.13 | 0.99 | 3.14 |
| 60 | | | 0.83 | 3.16 | 1.01 | 3.08 | 0.98 | 3.08 |
| 79 | | | 0.81 | 3.18 | 1.00 | 3.09 | 0.98 | 3.10 |
| 92 | | | 0.79 | 3.18 | 1.00 | 3.09 | 0.95 | 3.10 |
| 96 | | | 0.78* | 3.19 | | | | |
| 106 | | | | | 0.97 | 3.09 | 0.91 | 3.12 |
| 120 | | | | | 0.95 | 3.10 | 0.89 | 3.13 |
| 131 | | | | | 0.94 | 3.14 | 0.87 | 3.16 |
| 144 | | | | | 0.89 | 3.11 | 0.84 | 3.14 |
| 157 | | | | | 0.84 | 3.19 | 0.81 | 3.20 |
| 169 | | | | | 0.79 | 3.22 | 0.79 | 3.22 |
| 183 | | | | | 0.79 | 3.20 | 0.79 | 3.21 |
| 198 | | | | | 0.75* | 3.19 | 0.74* | 3.21 |

*Disappearance of malate spot on paper chromatogram

As the above table indicates, with the Chardonnay wine prepared which is a relatively highly acid wine, malolactic fermentation was essentially complete in the case of a wine sample inoculated with Er1a bacterial culture at 50 days, in the case of inoculation with Ey2d bacterial culture at 96 days. In the case of bacterial cultures prepared from ML-34 and PSU-1, malolactic fermentation was complete at the end of 198 days.

BIBLIOGRAPHY

Amachi, T. 1975. Chemical structure of a growth factor (TJF) and its physiological significance for malo-lactic bacteria, p. 103–108. In: J. G. Carr, C. V. Cutting, and G. C. Whiting (eds.), Lactic Acid Bacteria in Beverages and Food. Academic Press, London and New York.

Amachi, T. and Yoshizumi, H. 1969. Studies on the bacteria isolated from wine. Part V. Isolation and properties of the growth factor from tomato juice for a bacterium inducing malo-lactic fermentation. Agr. Biol. Chem. 33:139–146.

Beelman, R. B., Gavin III, A. and Keen, R. M. 1977. A new strain of Leuconostoc oenos for induced malo-lactic fermentation in eastern wines. Am. J. Enol. Vitic. 28:159–165.

Beelman, R. B., McArdle, F. J. and Duke, G. R. 1980. Comparison of Leuconostoc oenos strains ML34 and PSU-1 to induce malo-lactic fermentation in Pennsylvania red table wines. Am. J. Enol. Vitic. 31:269–276.

Garvie, E. I. 1967. The growth factor and amino acid requirements of species of the genus Leuconostoc including L. paramesenteroides (sp. nov) and L. oenos. J. Gen. Microbiol. 48:439–447.

Garvie, E. I. and Mabbit, L. A. 1967. Stimulation of the growth of Leuconostoc oenos by tomato juice. Arch. Mikrobiol. 55:398–407.

Ingraham, J. L., Vaughn, R. H. and Cooke, G. M. 1960. Studies on the malo-lactic organisms isolated from California wines. Am. J. Enol. Vitic. 11:1–4.

Kunkee, R. E. Simplified Chromatographic Procedure for Detection of Malo-lactic Fermentation. Wines & Vines. pp 23–24. March, 1968.

Kunkee, R. E. 1967. Malo-lactic fermentation. Adv. Appl. Microbiol. 9:235–279.

Martley, F. G. 1972. The effect of cell numbers in streptococcal chains on plate-counting. New Zealand J. Dairy Sci. Technol. 7:7–11.

McCloskey, L. P. Enzymatic Assay for Malic-Acid and Malo-lactic Fermentations. Am. J. Enol. Vitic. 31 (3): 212–215. 1980.

Pilone, G. J. and Kunkee, R. E. 1972. Characterization and energetics of Leuconostoc oenos ML34. Am. J. Enol. Vitic. 23:61–70.

Radler, F. 1975. The metabolism of organic acids by lactic acid bacteria, p. 17–27. In: J. G. Carr, C. V. Cutting, and G. C. Whiting, (eds.), Lactic Acid Bacteria in Beverages and Food. Academic Press, New York and London.

Yoshizumi, H. 1975. A malo-lactic bacterium and its growth factor. p. 87–102. In: J. G. Carr, C. V. Cutting and G. C. Whiting. (eds.) Lactic Acid Bacteria in Beverages and Food. Academic Press, New York and London.

It is claimed and desired to secure by Letters Patent:

1. Biologically pure cultures of strains of Leuconostoc oenos having assigned depository numbers ATCC39401 or ATCC39402, characterized by an ability in wines of relatively high acidity inoculated with the strains to carry out faster malolactic fermentation than results with commercially available strains ML-34 and PSU-1.

2. In the making of wine, the method comprising inoculating the wine with a biologically pure culture of strains of Leuconostoc oenos selected from the group consisting of those having assigned depository numbers ATCC39401 and ATCC39402, and producing malolactic fermentation in the wine with the bacteria strain inoculated.

* * * * *